US008958946B2

(12) United States Patent
Nicq et al.

(10) Patent No.: US 8,958,946 B2
(45) Date of Patent: *Feb. 17, 2015

(54) SYSTEM FOR DETECTING DEFECTS ON AN AIRCRAFT ENGINE IMPELLER WHEEL

(71) Applicant: SNECMA, Paris (FR)

(72) Inventors: Geoffroy Nicq, Thomery (FR); Valerio Gerez, Yerres (FR)

(73) Assignee: SNECMA, Paris (FR)

( * ) Notice: Subject to any disclaimer, the term of this patent is extended or adjusted under 35 U.S.C. 154(b) by 60 days.

This patent is subject to a terminal disclaimer.

(21) Appl. No.: 13/792,537

(22) Filed: Mar. 11, 2013

(65) Prior Publication Data

US 2013/0239653 A1    Sep. 19, 2013

(30) Foreign Application Priority Data

Mar. 13, 2012    (FR) .................................. 12 52250

(51) Int. Cl.
| | | |
|---|---|---|
| G06F 7/00 | (2006.01) | |
| G01N 3/30 | (2006.01) | |
| F01D 21/00 | (2006.01) | |
| F01D 21/14 | (2006.01) | |

(52) U.S. Cl.
CPC ............. G01N 3/30 (2013.01); F01D 21/003 (2013.01); F01D 21/14 (2013.01)
USPC ...................................................... 701/34.4

(58) Field of Classification Search
CPC ................... B32B 17/10954; B65G 2249/04; B65G 49/068; B65G 57/11; F01D 21/003; F01D 21/14; F01D 21/04; G01N 3/30

USPC ........................................................ 701/34.4
See application file for complete search history.

(56) References Cited

U.S. PATENT DOCUMENTS

| | | | | |
|---|---|---|---|---|
| 3,597,963 | A  * | 8/1971 | Smejkal et al. .................. | 73/660 |
| 8,386,244 | B2 * | 2/2013 | Ricci et al. ..................... | 704/205 |
| 8,602,734 | B2 * | 12/2013 | Philippot ..................... | 416/97 R |
| 2006/0200035 | A1 * | 9/2006 | Ricci et al. ..................... | 600/513 |
| 2006/0245500 | A1 * | 11/2006 | Yonovitz .................. | 375/240.19 |
| 2011/0027103 | A1 * | 2/2011 | Philippot ..................... | 416/97 R |

(Continued)

FOREIGN PATENT DOCUMENTS

| | | | |
|---|---|---|---|
| EP | 1 312 766 A2 | 5/2003 | |
| EP | 1 367 226 A1 | 12/2003 | |

(Continued)

OTHER PUBLICATIONS

U.S. Appl. No. 13/754,186, filed Jan. 30, 2013, Tourin, et al.

(Continued)

*Primary Examiner* — McDieunel Marc
(74) *Attorney, Agent, or Firm* — Oblon, Spivak, McClelland, Maier & Neustadt, L.L.P.

(57) ABSTRACT

A method and an on-board system for detecting impact on an impeller wheel of an aircraft engine. Deflection signals representative of the deflections on the blades of the impeller wheel are acquired. Each of the deflection signals is correlated with a pulse signal typical of an impact on a sound blade at the rotation frequency of the engine, in order to identify impacts on the impeller wheel. The impact signals are extracted from among the deflection signals. The impact signals are transmitted to the ground in order that the signals are analyzed to detect defects on the blades of the impeller wheel.

11 Claims, 2 Drawing Sheets

(56) References Cited

U.S. PATENT DOCUMENTS

2011/0164785 A1* 7/2011 Yonovitz .................. 382/103
2011/0313760 A1* 12/2011 Ricci et al. ................ 704/211
2013/0197747 A1* 8/2013 Tourin et al. .............. 701/34.4
2013/0211768 A1 8/2013 Gerez et al.

FOREIGN PATENT DOCUMENTS

| GB | 2 374 670 A | 10/2002 |
|---|---|---|
| GB | 2 437 391 A | 10/2007 |
| GB | 2485891 A | 5/2012 |
| WO | WO 2010/051128 A1 | 5/2010 |
| WO | WO 2011/095737 A1 | 8/2011 |

OTHER PUBLICATIONS

French Preliminary Report issued Nov. 14, 2012 in Patent Application No. 1252250 with English Translation of Category of Cited Documents.

United Kingdom Search Report issued May 23, 2013 in Patent Application No. 1304297.3.

* cited by examiner

SYSTEM FOR DETECTING DEFECTS ON AN AIRCRAFT ENGINE IMPELLER WHEEL

TECHNICAL FIELD

The present invention relates to the field of engine surveillance systems and, more particularly, the detection of defects on an impeller wheel of an aircraft engine.

PRIOR ART

An aircraft engine comprises several impeller wheels that are potentially exposed to undergoing impacts that can damage them and, consequently, affect the correct operation of the engine.

In most cases, the impact is not noticed by the pilot during the flight and the finding on the blade is made during the control of the airplane just before taking off again. This constitutes the main cause of flight D&C (Delays and Cancellation).

Methods exist for detecting impact on the blades, and particularly the blades of the fan. From these detections may be deduced impact breakdowns, which can help to issue warnings to bring about a visual or mechanical inspection of the blades.

A visual inspection can only be carried out on blades that are visible, or which may be accessed via endoscopy. In this case, the change of a blade only occurs after an incident when the defect is sufficiently visible to be noticed.

Furthermore, methods exist for detecting structural defects (cracks, shape defects) that can be carried out by modal analysis on the structural part. However, these methods do not apply to on-board rotating systems because they require a costly instrumentation which has to be partially supported by the rotors, leading to a complex implementation. In fact, this necessitates a pulse source and a sensor to be mounted on the rotor, from whence a complex implementation to supply the turning part with command, power and detection signals. Another solution would be to embark in the turning part all the control electronics, which is complicated given the thermal and vibratory environment.

The aim of the present invention is consequently to propose a system and a method of detection that is simple to implement and which is capable of detecting with precision and reliability defects on an impeller wheel of an engine without having the aforementioned drawbacks.

DESCRIPTION OF THE INVENTION

The present invention is defined by a method for detecting defects on an impeller wheel of an aircraft engine, comprising the following steps:
  acquisition of deflection signals representative of the deflections on the blades of said impeller wheel,
  identification of impact by correlations of each of said deflection signals with a detection pulse signal typical of an impact on a sound blade at the rotation frequency of the engine,
  extraction of the impact signals from among said deflection signals,
  application of a modal analysis to each of said impact signals to identify the modal parameters relative to each impacted blade, and
  monitoring the evolution of said modal parameters in order to detect defects on said blades.

By uniquely monitoring the impact signals, this method makes it possible to make more reliable the diagnostic by detecting structural defects not visible by inspection while reducing the computational load and while facilitating the implementation of the solution. It will be noted that the monitoring of the soundness of the blades based on an impact signal improves the signal/noise ratio and increases the quality of the detection of defects. In addition, the invention takes advantage of the "Tip timing" method (spot measurement analysis method) already used in the engine and requiring no mounting of pulse source or specific electronics in the engine.

Advantageously, said steps of acquisition, identification and extraction are carried out on-board the aircraft whereas the steps of modal analysis and monitoring of the modal parameters are carried out on the ground.

This makes it possible to separate the operations of on-board signal processing requiring little calculation time and those of modal analysis and monitoring requiring more calculation. Thus, it is possible to reduce the computational load on-board the aircraft while enabling a reliable and precise detection of defects and facilitating any later evolution of the detection method.

Advantageously, said impact signals are transmitted to the ground and/or saved in a storage means.

Thus, the method makes it possible to record or to transmit to the ground just small time windows around impacts that have been identified by correlation. This makes it possible to economise the memory space and/or the transmission costs.

Advantageously, the impact identification step comprises a first correlation carried out in an independent manner on each blade to identify the blade impacted first and a second correlation to identify successive blade impacts.

This makes it possible to increase the probability of the detection of impact.

Advantageously, the method comprises a validation of the modal parameters identified for each impacted blade by reconstituting for said blade a reconstitution pulse signal and by correlating said reconstitution pulse signal with the impact signal relative to said impacted blade.

This makes it possible to verify the modal analysis and to validate the modal parameters and thus to characterise each blade by its vibration frequency and the absorption of the vibrations.

Advantageously, the method comprises a comparison of said validated modal parameters with those of sound blades in order to measure shifts of these parameters.

This enables the state of each blade to be diagnosed.

Advantageously, said comparison is carried out from impact to impact to analyse the evolution of the modal parameters and the number of impacts.

Thus, a shift of the vibration frequency or an increase in the shock absorption of a blade foretells the beginning of a crack on the blade.

Advantageously, the method comprises a storage of said validated modal parameters in a database specific to the impeller wheel.

This makes it possible to compare the modal parameters from impact to impact in order to easily search for anomalies revealing the appearance of defects on the blades.

The invention also relates to an on-board system for detecting impact on an impeller wheel of an aircraft engine, comprising:
  acquisition means for acquiring deflection signals representative of the deflections on the blades of said impeller wheel,
  calculation means for correlating each of said deflection signals with a pulse signal typical of an impact on a sound blade at the rotation frequency of the engine, in order to identify impacts on the impeller wheel, calculation means for extracting the impact signals from among said deflection signals, and transmission means for transmitting said impact signals to the ground in order that said signals are analysed to detect defects on the blades of the impeller wheel.

The invention also relates to an aircraft engine comprising an on-board detection system according to the above characteristics.

The invention also relates to an analysis system for the detection of defects on an impeller wheel of an aircraft engine, comprising:

reception means for receiving impact signals from an on-board detection system according to the above characteristics, processing means for applying a modal analysis to each of said impact signals in order to identify the modal parameters relative to each impacted blade, and processing means for monitoring the evolution of said modal parameters in order to detect irregularities in their evolution revealing defects on the blades of the impeller wheel.

BRIEF DESCRIPTION OF DRAWINGS

Other characteristics and advantages of the invention will become clear on reading the preferential embodiments of the invention made with reference to the appended figures, among which.

DETAILED DESCRIPTION OF PARTICULAR EMBODIMENTS

The basic concept of the invention is based on the detection of defects and beginnings of cracks on the blades of an impeller wheel by taking advantage of a detection system of "tip timing" type already used for the characterisation of turning components and the impacts generated by objects sucked into the engine. Thus, the present invention does not require a pulse source to be mounted on the engine, and no specific electronics.

Figure 1:
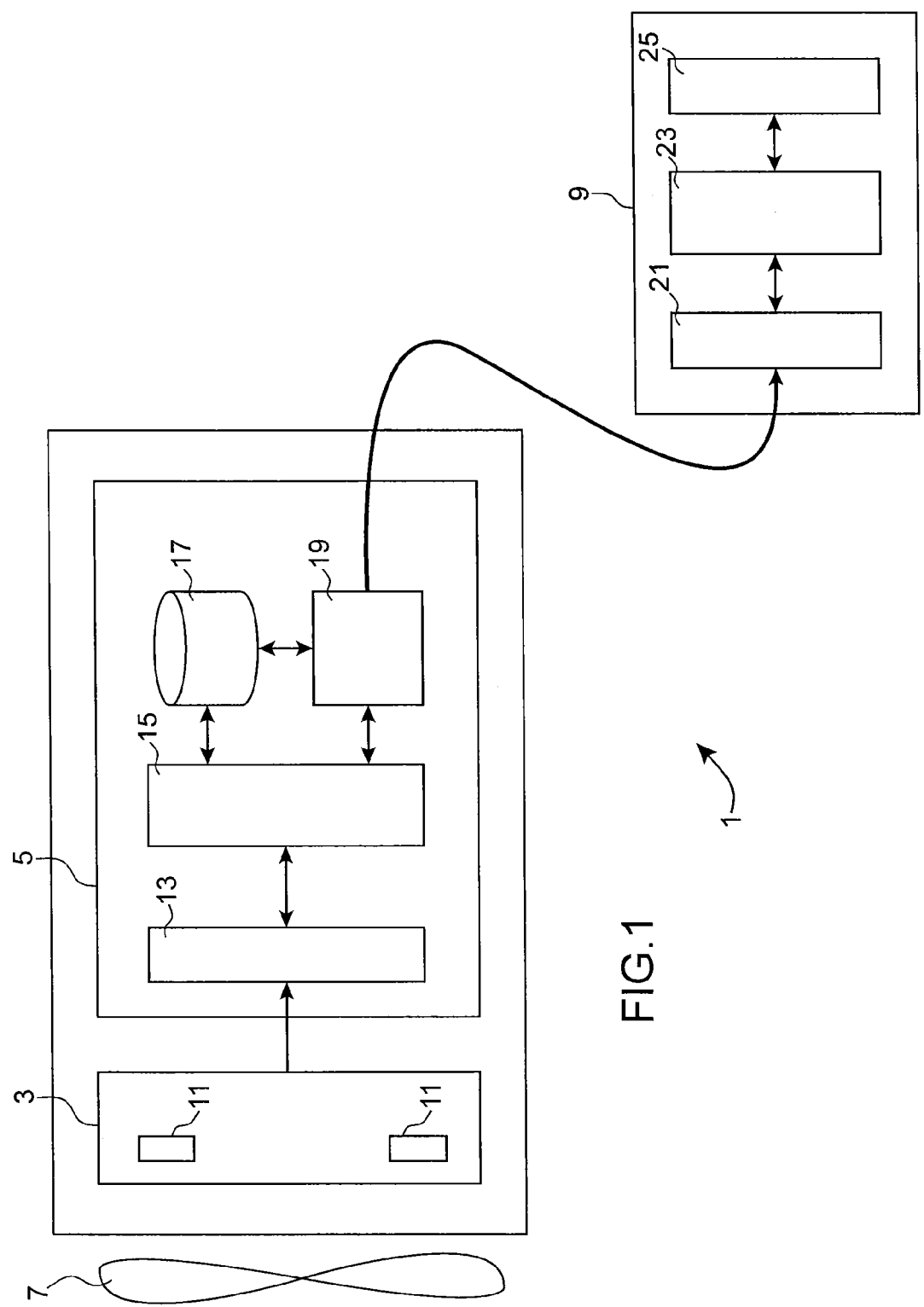
FIG. 1 illustrates in a schematic manner an aircraft engine surveillance system, according to the invention.

FIG. 1 illustrates in a schematic manner an aircraft engine surveillance system, according to the invention.

The surveillance system 1 comprises a measuring system 3, an on-board system 5 for detecting an impact on an impeller wheel 7 of the engine (not represented), and an analysis system 9 on the ground for detecting defects on the impeller wheel 7.

The impeller wheel 7 may be that of a fan or that of a high pressure (HP) compressor or that of any other component of the engine.

The measuring system 3 already exists in the engine and comprises one or more sensors 11 giving information on the revolutions per minute of the engine and potential deflections on the blades or paddles.

The time signals of deflections are obtained according to, for example, an operation of "Tip Timing" type in association with at least one sensor 11 installed in line with the impeller wheel 7. In normal operation, without impacts, the blades are going to pass in front of the sensor 11 in a regular manner and the time interval measured between the passage of two consecutive blades is constant at a given engine speed thereby defining a reference time signal. Any modification of the position of a blade at the moment when it passes in front of the sensor 11 in relation to its reference position is thus indicative of a deflection of the blade.

By way of example, the sensor 11 may be a Foucault current sensor or a sensor of capacitive type. These kinds of sensors are robust, precise, not very bulky and do not require specific cleaning.

Furthermore, it will be noted that the engine speed may be acquired either in a direct manner thanks to a dedicated sensor 11 coupled to a phonic wheel or according to the Tip Timing method. In fact, an impeller wheel is almost in itself a phonic wheel and the revolutions per minute may be determined from the passage of the blades. Thus, the use of the "Tip Timing" operation makes it possible both to monitor the blades and to determine the revolutions per minute of the engine.

Furthermore, the detection system 5 comprises data acquisition means 13, calculation means 15, storage means 17, and transmission means 19.

The acquisition means 13 are configured to acquire from the measuring system 3, the revolutions per minute (or frequency) of the engine as well as a series of deflection signals representative of the deflections on the blades of the impeller wheel 7 at said revolutions per minute.

According to the invention, the calculation means 15 are configured to correlate each of the deflection signals with a pulse signal typical of an impact on a sound blade at the rotation frequency of the engine, in order to identify impacts on the impeller wheel 7.

The pulse signal is a sort of oscillatory signature limited in time and representative of an impact. In fact, in the case of shock on a blade, it vibrates on these specific modes, this vibration which is absorbed in several engine revolutions is represented by the pulse signal. The latter may be defined by a sort of wavelet or pseudo-wavelet having the shape of an oscillatory wave, the amplitude of which starts at zero, increases over a small time frame, and then decreases to return to zero according to for example a decreasing exponential.

The correlation between the deflection signals and the pulse signal makes it possible to detect automatically any impact on the impeller wheel 7 whatever the weight of the ingested object. In other words, the correlation makes it possible to detect the impacts not felt by the pilot in addition to those felt by him. In addition, when an impact is detected, a classification over time of the detection signals makes it possible to indicate the order of these impacts and to identify the blade impacted first.

Moreover, the calculation means 15 are configured to extract the impact signals from among the deflection signals. Thus, only the impact signals and numbers of blades impacted will be stored in the storage means 15 and/or transmitted to the ground by the transmission means 19.

In fact, the transmission means 19 are configured to transmit the impact signals to the analysis system 9 on the ground in order that the latter analyses them systematically with a view to detecting defects on the blades of the impeller wheel.

Advantageously, the transmission of the impact signals to the analysis system 9 on the ground may take place automatically via a transmission of SATCOM or GSM type using the ACARS data transmission system of the aircraft.

In a variant, the transmission of the data to the analysis system 9 can take place manually when the aircraft is on the ground by connection of a data bus to recover the impact signals saved in the storage means 15 of the detection system 5.

It will be noted that the detection system 5 may be incorporated in a specific box or form part of an existing electronics box. Advantageously, it is possible to exploit the acquisition and processing means of an on-board calculator in the aircraft or in a calculator incorporated in the aircraft engine of EMU (Engine Monitoring Unit) type to exploit the impact detection system according to the invention. In particular, the calculator may be used to run a computer programme saved in storage means of the calculator and comprising code instructions for implementing the impact detection method according to the invention.

Furthermore, the analysis system 9 on the ground comprises reception means 21, processing means 23, and data base (or BDD for database) storage means 25.

The reception means 21 are configured to receive the impact signals from the on-board detection system 5.

After the reception of the impact signals, the processing means 23 apply a modal analysis to each of said signals in order to identify modal parameters relative to each impacted blade. The modal analysis makes it possible to determine the specific frequency and shock absorption on each impact. The processing means 23 then carry out the validation of the modal parameters identified for each impacted blade before saving them in a database 23 specific to the impeller wheel 7.

The processing means 23 are also configured to monitor the evolution of the modal parameters in order to detect potential irregularities in their evolution revealing defects on the blades of the impeller wheel 7. In particular, the processing means 23 compare the modal parameters with a database of sound blades in order to estimate the shifts in frequency and shock absorption. This comparison is carried out from impact to impact to analyse the evolution of modal parameters, the number of impacts and potentially other characteristics relative to the impacts. Thus, in the event where a defect is detected, the processing means 23 generate a message or a maintenance notification of the engine comprising the identification data of the defective blade (or blades).

Figure 2:
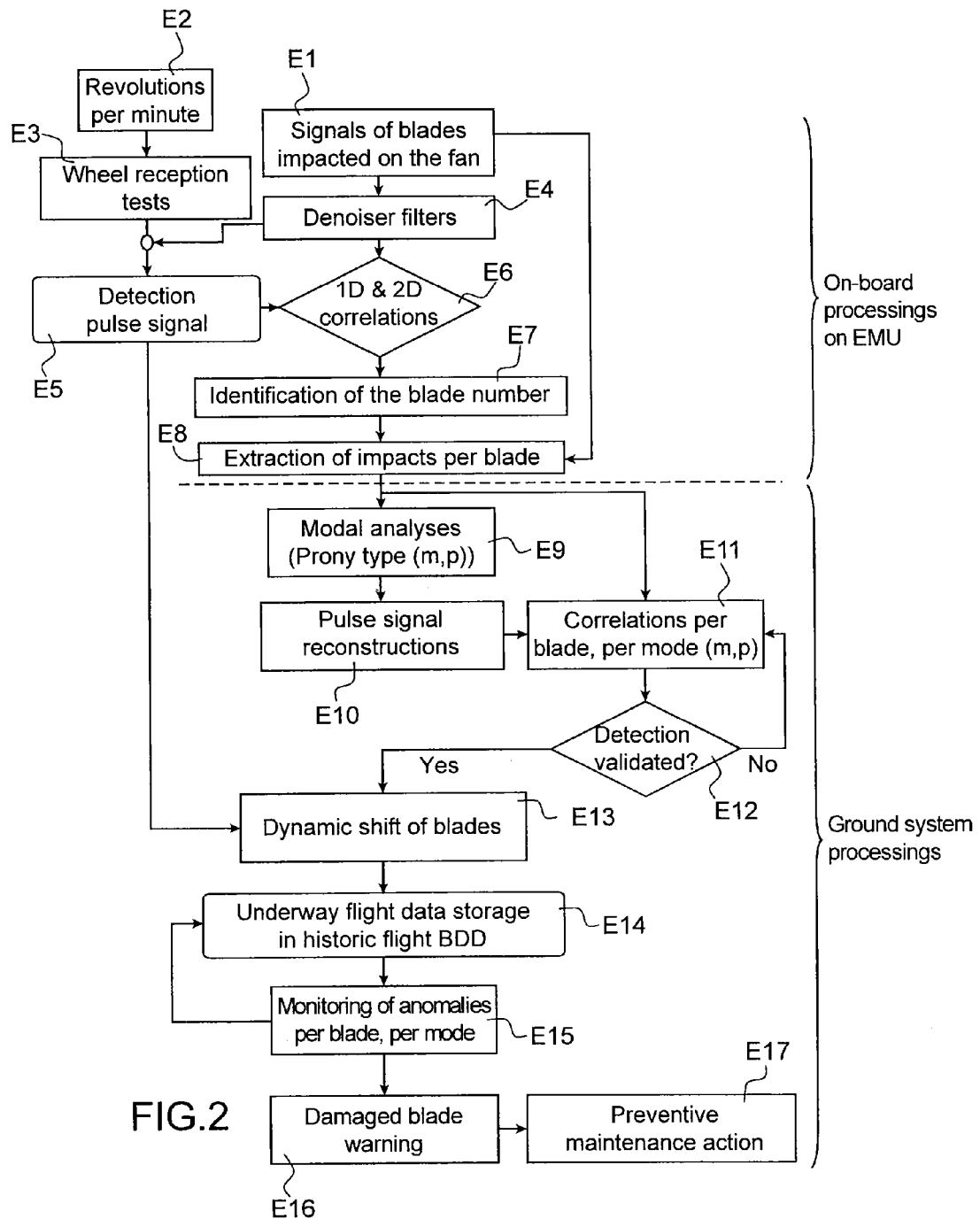
FIG. 2 is a block logic diagram illustrating a preferred embodiment of the surveillance, according to the invention.

FIG. 2 is a block logic diagram illustrating a preferred embodiment of the surveillance system, according to the invention. This figure is also an illustration of the steps of the method for detecting defects on an impeller wheel of an aircraft engine, according to the invention.

Advantageously, blocks E1 to E8 correspond to on-board processings whereas blocks E9 to E17 correspond to processings on the ground. The on-board processings are limited to a single detection and/or harmonic qualification of the impact signals and may be implemented by a scaled down and proven on-board instrumentation (for example, the EMU).

Blocks E1 and E2 relate to the time acquisition of deflection signals representative of the deflections on the blades (or paddles) as well as the acquisition of the revolutions per minute of an impeller wheel.

More particularly, block E1 relates to the reading of the deflection signals of all the blades of the impeller wheel and block E2 relates to the reading of the revolutions per minute corresponding to the deflection signals read at block E1.

Blocks E3 to E7 explain with more details the identification of the impacts.

Block E3 is a reception test of the blades. This test stems from customary production quality control tests carried out on a blade or a family of blades to verify that there have been no manufacturing defects.

Thus, one may construct for each blade or family of blades a catalogue or a predetermined series of detection pulse signals representing impacts absorbed on a blade according to different revolutions per minute of the engine. In other words, each pulse signal is a signature of an impact absorbed on the first bending mode of a blade as a function of the revolutions per minute.

It will be noted that the series of detection pulse signals is constructed beforehand from an impact detection model and/or bench tests. Advantageously, said pulse signals are obtained firstly by calculations, then refined by tests.

Thus, at block E4, a detection pulse signal is selected from among the series of pulse signals each corresponding to a signature representative of an impact absorbed on a sound blade as a function of the revolutions per minute. The revolutions per minute may thus be used as a selection parameter for choosing as signature the pulse signal corresponding to said revolutions per minute. Advantageously, this makes it possible to take account of the fact that the specific frequency of the blade can vary as a function of the revolutions per minute. In fact, the shape of the blade may change (for example, the blade untwists) under the effect of a centrifugal force thereby bringing about an evolution of the specific frequency of the blade as a function of the rotation of the engine.

At block E5, the deflection signals as well as the pulse signal are filtered according to predetermined parameters to centre said signals on zero. The same filtration parameters are chosen to filter the pulse signal and the deflection signals in order to enable the signature to resemble as closely as possible the impact present in the deflection signals.

Advantageously, isolated or aberrant data (outliers) potentially present in the deflection signals, which may be due, for example, to electrical shocks or random errors, are also eliminated.

Thus, one has at the output of blocks E4 and E5 filtered deflection signals and a detection pulse signal.

At block E6, the calculation means 15 carry out correlations between the deflection signals and the detection pulse signal.

Advantageously, the calculation means carry out a first 1D correlation performed in an independent manner on each blade to identify the blade impacted first and a second 2D correlation to identify successive blade impacts.

The first correlation consists for a given blade in calculating for example the convolution product between the deflection signal relative to said blade and the detection pulse signal. This operation is carried out as many times as there are blades present on the impeller wheel. Advantageously, the convolution product is normalised to overcome the amplitude of the impact and to recognise the latter uniquely on the shape due to the specific pseudo-frequency and to the shock absorption (both being known). The closer the normalised score of the convolution product approaches 1, the higher the detection probability.

The second correlation consists for example in calculating the convolution product between the detection pulse signal and each of the deflection signals relative to the blades neighbouring that which has undergone the first impact. This makes it possible to isolate successive impacts and increase the probability of detection. In fact, the impact on a blade generates debris that is going to impact the neighbouring blades. It will be noted that if the second correlations on the neighbouring blades do not detect impacts, one may reasonably deduce that the first impact signal corresponds to an electrical pulse or to an environment noise and not the result of a real impact on the blade.

Thus, block E7 concerns the identification of the blades impacted and the resetting on successive blade impacts. The identification of an impact may be carried out by verifying whether the result of the correlation exceeds a predetermined detection threshold. This detection threshold may be adjusted through experimentation and/or operational feedback.

Block E8 relates to the extraction of the non-filtered impact signals from among the deflection signals of block E1. It will be noted that the extraction is carried out from unprocessed deflection signals before filtering in order not to corrupt them by the filter.

The impact signals thus extracted are saved in a storage means 17 and/or automatically transmitted to the ground.

Thus, instead of transmitting all of the deflection signals, one is going to extract just small time windows around the impacts that have been identified by correlation thus reducing the quantity of information transmitted to the ground.

At step E9, a modal analysis is applied to each of the impact signals from the aircraft to identify modal parameters relative to each impacted blade. Conventional modal analysis methods (for example, of Prony type) may be used to determine specific frequencies $m_i$ and shock absorption $p_i$ on each impact.

Generally speaking, the modal analysis may give several solutions, in other words, several couples $(m_1, p_1), \ldots, (m_n, p_n)$ for each impact signal. Nevertheless, there can only be a single valid couple of modal parameters for each impact signal. Consequently, a small loop (blocks E10-E12) is used in order to validate the modal parameters corresponding to each impacted blade.

Thus, for a given impacted blade, at block E10, a reconstitution pulse signal is constructed for each couple of modal parameters $(m_i, p_i)$ relative to said given blade. In fact, knowing the specific frequency and the shock absorption, it is easy to reconstitute a pulse signal of damped sinusoidal shape.

At block E11, one calculates in an iterative manner, for the different couples of modal parameters, the correlation between each reconstitution pulse signal corresponding to each couple of modal parameters and the original impact signal relative to said given impacted blade.

Block E12 is a test for validating the couples of modal parameters according to the result of the correlation of block E11. Thus, if the correlation of the preceding step is high (for example, above a predetermined validation threshold), one validates the corresponding couple of modal parameters and one passes to block E13. If not, in other words if the correlation is low, one passes to a following couple of modal parameters and re-loops at block E11.

Blocks E11-E16 relate to the control and the monitoring of the evolution of the modal parameters with a view to detecting defects on the blades.

At block E13 one compares the modal parameters validated at block E12 with a database of parameters comprising the modal parameters of sound blades from block E5 in order to measure the shifts of said parameters. The database of parameters is in fact supplied by the acceptance tests carried out on the blades before mounting on the impeller wheel. It will be noted that the shifts may be defined by frequency and shock absorption differences between the impacted blade and the sound blade.

At block E14 the validated modal parameters are stored in a database specific to the impeller wheel 7. More generally, the data from the flight underway is stored in historic flight databases.

At block E15 one follows the shifts per blade and per mode and re-loops at block E14. Thus, a small and progressive shift may quite simply be considered as a normal ageing of the blade. Nevertheless, a sharp variation in the shift value relative to a given blade is an indication of the appearance of a defect (for example, a beginning of a crack) on said blade. More precisely, the validated modal parameters are compared from impact to impact by a learning and anomalies detection algorithm of "trend monitoring" type. The anomaly detection is based on the evolution of the dynamic parameters (specific frequency, shock absorption) and potentially on a quantification (number, energy, etc.) of the impacts.

At block E16 a warning according to the anomaly detected at block E15 is emitted.

Finally, at block E17, the reception of an alarm enables the triggering of a preventive maintenance action for a visual and mechanical inspection of the incriminated blades and for a potential change of blades.

The invention claimed is:

1. A method for detecting defects on an impeller wheel of an aircraft engine for an aircraft, said method comprising:
    acquiring deflection signals representative of deflections on blades of said impeller wheel,
    identifying impact by correlating each of said deflection signals with a detection pulse signal typical of an impact on a sound blade at a rotation frequency of the engine,
    extracting impact signals from among said deflection signals,
    applying a modal analysis to each of said impact signals to identify modal parameters relative to each impacted blade, and
    monitoring an evolution of said modal parameters in order to detect defects on said blades.

2. The method according to claim 1, wherein said acquiring, said identifying and said extracting are carried out on-board the aircraft whereas applying said modal analysis and said monitoring of the modal parameters are carried out on the ground.

3. The method according to claim 1, wherein said impact signals are transmitted to the ground and/or saved in a storage device.

4. The method according to claim 1, wherein said identifying comprises a first correlation carried out in an independent manner on each blade to identify the blade impacted first and a second correlation to identify successive blade impacts.

5. The method according to claim 1, further comprising validating the modal parameters identified for each impacted blade by reconstituting for said blade a reconstitution pulse signal and by correlating said reconstitution pulse signal with the impact signal relative to said impacted blade.

6. The method according to claim 5, further comprising comparing said modal parameters validated with modal parameters of sound blades in order to measure drifts of said parameters.

7. The method according to claim 6, wherein comparing is carried out from impact to impact to analyse the evolution of the modal parameters and the number of impacts.

8. The method according to claim 5, further comprising storing said validated modal parameters in a database specific to the impeller wheel.

9. An on-board system for detecting impact on an impeller wheel of an engine for an aircraft, said system comprising:
    an acquisition device for acquiring deflection signals representative of deflections on blades of said impeller wheel,
    a correlation device for correlating each of said deflection signals with a pulse signal typical of an impact on a sound blade at the rotation frequency of the engine, in order to identify impacts on the impeller wheel,
    a calculation device for extracting impact signals from among said deflection signals, and
    a transmission device for transmitting said impact signals to the ground in order that said signals are analysed to detect defects on the blades of the impeller wheel.

10. An aircraft engine comprising an on-board detection system according to claim 9.

11. An analysis system for the detection of defects on an impeller wheel of an engine for an aircraft, said system comprising:
- a reception device for receiving impact signals from an on-board detection system according to claim 9, and
- a processor configured to apply a modal analysis to each of said impact signals in order to identify the modal parameters relative to each impacted blade,
- wherein said processor is further configured to monitor an evolution of said modal parameters in order to detect irregularities in their evolution revealing defects on the blades of the impeller wheel.

* * * * *